United States Patent
Bluma et al.

(10) Patent No.: US 12,180,452 B2
(45) Date of Patent: Dec. 31, 2024

(54) BIOREACTOR COMPRISING A FILTER POCKET, AND METHOD FOR PRODUCING SAME

(71) Applicant: Sartorius Stedim Biotech GmbH, Goettingen (DE)

(72) Inventors: Arne Bluma, Goettingen (DE); Franziska Faulstich, Goettingen (DE); Fabian Tunzini, Tagelswangen (CH); Rachel Delessert, Tagelswangen (CH); Darius Tuor, Tagelswangen (CH)

(73) Assignee: SARTORIUS STEDIM BIOTECH GMBH (DE)

( * ) Notice: Subject to any disclaimer, the term of this patent is extended or adjusted under 35 U.S.C. 154(b) by 792 days.

(21) Appl. No.: 17/421,601

(22) PCT Filed: Dec. 19, 2019

(86) PCT No.: PCT/EP2019/086465
§ 371 (c)(1),
(2) Date: Jul. 8, 2021

(87) PCT Pub. No.: WO2020/144049
PCT Pub. Date: Jul. 16, 2020

(65) Prior Publication Data
US 2022/0119753 A1    Apr. 21, 2022

(30) Foreign Application Priority Data
Jan. 9, 2019    (DE) .................... 10 2019 100 434.9

(51) Int. Cl.
| | |
|---|---|
| *C12M 1/00* | (2006.01) |
| *B01D 61/14* | (2006.01) |
| *B01D 63/08* | (2006.01) |
| *B01D 71/68* | (2006.01) |

(52) U.S. Cl.
CPC ........... *C12M 29/10* (2013.01); *B01D 61/147* (2013.01); *B01D 63/081* (2013.01); *B01D 71/68* (2013.01);
(Continued)

(58) Field of Classification Search
None
See application file for complete search history.

(56) References Cited

U.S. PATENT DOCUMENTS

| 8,932,843 B2 | 1/2015 | Niazi |
|---|---|---|
| 9,017,997 B2 | 4/2015 | Wuenn et al. |

(Continued)

FOREIGN PATENT DOCUMENTS

| EP | 1132460 A2 | 9/2001 |
|---|---|---|
| EP | 2268788 B1 | 7/2016 |

(Continued)

OTHER PUBLICATIONS

Machine-generated English translation (Year: 2006).*
International Search Report Issued in International Application No. PCT/EP2019/086465, Issued Apr. 29, 2020, 2 pages.

*Primary Examiner* — P. Kathryn Wright
(74) *Attorney, Agent, or Firm* — Dilworth IP, LLC

(57) ABSTRACT

A bioreactor for cultivating microorganisms and cells of animal or plant origin includes a filter pocket which is arranged on the inner surface of a flexible wall of the bioreactor and which is delimited on the outside by the wall of the bioreactor and on the inside by a filter pocket wall. The inside filter pocket wall is formed at least partially by a filter medium. A spacer is arranged in the filter pocket between the wall of the bioreactor and the filter medium. The spacer has at least one through opening. A connecting portion of the filter medium protrudes through the through opening and is directly connected to the wall of the bioreactor. A method of manufacturing a filter pocket in a (Continued)

bioreactor for cultivating microorganisms and cells of animal or plant origin is also provided herein.

16 Claims, 2 Drawing Sheets

(52) U.S. Cl.
CPC ............ *C12M 23/26* (2013.01); *C12M 23/28* (2013.01); *C12M 29/04* (2013.01); *B01D 2313/146* (2013.01)

(56) References Cited

U.S. PATENT DOCUMENTS

| | | |
|---|---|---|
| 2009/0325282 A1 | 12/2009 | Bungay, III |
| 2012/0016113 A1 | 1/2012 | Niazi |
| 2012/0238011 A1* | 9/2012 | Tuohey .................. C12M 25/16 435/297.1 |
| 2013/0081995 A1* | 4/2013 | Larsen .................. B01D 35/027 210/443 |
| 2014/0011270 A1 | 1/2014 | Chotteau et al. |
| 2014/0287512 A1 | 9/2014 | Kaisermayer et al. |
| 2016/0194589 A1 | 7/2016 | Liderfelt et al. |
| 2018/0346864 A1 | 12/2018 | Faldt |

FOREIGN PATENT DOCUMENTS

| | | | |
|---|---|---|---|
| JP | 2014527808 A | 10/2014 | |
| KR | 20060019241 A * | 3/2006 | |
| WO | 2012158108 A1 | 11/2012 | |
| WO | WO-2017055059 A1 * | 4/2017 | ............ C12M 23/14 |
| WO | 2019001766 A1 | 1/2019 | |

* cited by examiner

BIOREACTOR COMPRISING A FILTER POCKET, AND METHOD FOR PRODUCING SAME

FIELD OF THE INVENTION

The invention relates to a bioreactor for cultivating microorganisms and cells of animal or plant origin. The invention further relates to a method of manufacturing a filter pocket of such a bioreactor.

BACKGROUND OF THE INVENTION

Document EP 2 268 788 B1 discloses a bioreactor formed as a flat single-use bag, in which at least one filter pocket is fixed to the liquid-wetted inner surface of a wall of the bioreactor. The filter pocket is formed by welding the edges of a hydrophilic filter medium onto the inner wall of the bioreactor, such that the continuous weld seam delimits a collection and/or distribution space between the filter medium and the inner wall of the bioreactor. The collection/distribution space is communicatively connected to at least one connection for a supply and/or discharge of media. A spacer in the form of a support fabric which prevents the filter medium from adhering to the bioreactor wall and thus the collection/distribution space from collapsing may be provided in the collection/distribution space. Such a bioreactor is suitable for perfusion, in particular as a single-use bioreactor for use on a tilting device ("rocking motion bag" or "rocker bag") and is commercially available in sizes from 2 to 50 liters (total volume, corresponding to up to 25 liters working volume). For larger volumes, the need arises to provide a bioreactor suitable for larger volumes due to the increasing mechanical stress acting on the filter pocket, among other things.

SUMMARY OF THE INVENTION

The object of the invention is to provide a bioreactor suitable for perfusion also for large volumes, in particular in the order of 100 or 200 liters (total volume) or also more.

This object is achieved by a bioreactor having the features of claim 1 and by a method having the features of claim 10. Advantageous and useful designs of the bioreactor according to the invention and the method according to the invention are specified in the associated subclaims.

The bioreactor for cultivating microorganisms and cells of animal or plant origin according to the invention, preferably a single-use bioreactor, comprises a filter pocket which is arranged on the inner surface of a flexible wall of the bioreactor and is delimited on the outside by the wall of the bioreactor and on the inside by a filter pocket wall. The inside filter pocket wall is formed at least partially by a filter medium. A spacer is arranged in the filter pocket between the wall of the bioreactor and the filter medium. According to the invention, the spacer has at least one through opening. A connecting portion of the filter medium protrudes through the through opening and is directly connected to the wall of the bioreactor.

The invention is based on several findings. First, tests have shown that in bioreactors having a total volume of 100 liters or more, an edge welding of the filter medium is no longer sufficient as the edge of the filter medium may be detached from the bioreactor wall. In such a case, the function of the filter pocket would no longer be ensured, as unfiltered medium from the bioreactor could also enter the filter pocket. The reason therefor is the large quantity of liquid and the weight thereof in the bioreactor, i.e., accordingly large forces act on the filter pocket due to the hydrostatic pressure alone. If the bioreactor is used on a tilting device, the stress of the filter pocket is additionally increased due to the sloshing medium and the resulting force impacts and frictional forces resulting from the relative motions.

Furthermore, it has been found that the preferred materials of the filter medium, the spacer and the bioreactor wall cannot easily be connected to each other. The manufacture of a group composed of a filter medium, a spacer and a bioreactor wall by welding is already problematic due to the significantly different melting points of the preferred materials, as far as a welding of these materials is possible at all. The same also applies to a bonding of the components or other types of connection.

The invention overcomes these difficulties in that only the filter medium is connected to the wall of the bioreactor. In addition to a circumferential fluid-tight edge connection of the filter medium to the bioreactor wall as known from the prior art, the invention additionally provides at least one point connection between the filter medium and the bioreactor wall in the central region of the filter pocket (i.e. not in the edge region thereof) for a further stabilization of the filter pocket, without the spacer arranged therebetween participating in this at least one connection, i.e. no direct connection is provided between the spacer and the filter medium or between the spacer and the bioreactor wall. According to the invention, this is achieved in that the spacer has at least one through opening, and a connecting portion of the filter medium protruding through the through opening is directly connected to the wall of the bioreactor. In this way, it is possible to disregard the spacer when creating further fastening points for the filter pocket, i.e., only the materials of the filter medium and of the bioreactor wall establish a connection.

A particularly advantageous side effect of the additional fastening of the filter pocket according to the invention is the fixed positioning of the spacer in the filter pocket by the connecting portions of the filter medium which protrude through the through openings of the spacer. Owing to the design according to the invention, this fixed positioning is realized automatically without welding, bonding or any other joining technique. This is particularly advantageous as the spacer does not mechanically deform, roll up, unfold or the like during use.

According to the preferred embodiment of the invention, a plurality of through openings are provided which are preferably arranged so as to be regularly distributed over the spacer. Accordingly, a connecting portion of the filter medium protrudes through each through opening in the spacer and is directly connected to the wall of the bioreactor. By a skillful choice of the number, arrangement, size and shape of the point-like connections, an optimum relationship can be achieved between a good stability of the filter pocket, the least possible interference with the distribution of the filtered medium in the filter pocket and the largest possible membrane surface which can be used freely by flow, in which the welded area is as small as possible compared to the total membrane surface.

In this context, an embodiment in which the filter pocket is free from completely or partially separated chambers is advantageous. This means that the connecting portions of the filter medium additionally fixed to the bioreactor wall are selected with regard to the number, arrangement, size and shape such that no dead spaces or similar are formed in the filter pocket. In particular, it is not advantageous to form completely or almost closed connecting lines by the arrangement of the point-shaped connecting portions, which would lead to completely or almost completely closed chambers within the filter pocket.

The invention is suitable with regard to materials which are preferred for specific perfusion processes, in particular for a bioreactor the wall of which is formed of polyethylene, among others, in combination with a filter medium in the form of a microfiltration membrane which is preferably formed at least partially of aliphatic polyamides, polysulfones and polyethersulfones, polyesters, polyvinylidene halides, acrylic polymers, acrylic copolymers and cellulose esters, particularly preferably of polyethersulphone. The microfiltration membrane is connected on at least one of its two sides to a porous planar structure, in particular to a polypropylene/polyethylene-polyethylene terephthalate-polypropylene/polyethylene laminate. These materials can easily be connected to each other, in particular by welding. The spacer not involved in the connection is preferably made of polyethylene terephthalate which cannot be connected to the aforementioned materials or which can only be connected thereto in an insufficient manner. In principle, further spacers of mechanically and chemically inert materials are possible, the swelling and shrinkage degree of which is so low that it does not negatively affect the function of the membrane.

To permit a simple supply and/or discharge of medium from the filter pocket, a connecting piece to which a hose line which leads out of the bioreactor can be connected is preferably inserted into the filter medium.

The advantages of the invention have the best effect in bioreactors having a maximum total volume of at least 50 liters, preferably 100 liters, 200 liters and up to 1000 liters, in particular in single-use bioreactors of this size which are intended for use on a tilting device.

The invention also provides a method of manufacturing a filter pocket in a bioreactor for cultivating microorganisms and cells of animal or plant origin, which comprises the following steps: providing a flexible wall for forming a bioreactor, a spacer, and a filter pocket wall formed at least partially by a filter medium, wherein the filter pocket wall has a greater superficial extent than the spacer; forming at least one through opening in the spacer which completely penetrates the spacer; placing the spacer on the inner surface of the lower wall of the bioreactor; placing the filter pocket wall on the spacer; circumferentially fixing the edge of the filter pocket projecting beyond the spacer to the wall of the bioreactor; passing a connecting portion of the filter medium through the through opening; and fixing the connecting portion of the filter medium directly to the wall of the bioreactor.

The manufacturing method according to the invention makes use of the finding that the spacer can easily be "perforated", and that later, the filter medium can be directly connected to the bioreactor wall through the through openings thus produced (preferably in the same step), without the spacer itself having to form a direct connection with the filter medium or the bioreactor wall. The cross-section of the produced hole in the spacer should respectively be slightly larger than the later connecting portion, i.e., the point or surface area of the direct connection between the filter medium and the bioreactor wall. When the filter medium is connected to the bioreactor wall, in particular by welding, it is thus ensured that the material of the spacer is not inadvertently also welded. The size of the hole thus ensures the strength of the connecting points or areas, and no holes can occur in use.

After the manufacture of the filter pocket according to the invention, the bioreactor is completed. It is here basically not important whether the bioreactor is substantially formed alone from the flexible wall along with the filter pocket, for example by folding the wall and connecting the superimposed free edge portions, or whether one or more further walls are connected to each other so as to form a bioreactor.

The fixing of the at least one connecting portion of the filter medium to the wall of the bioreactor is best performed by spot welding. Suitable installations are available on the market, and the connecting technique as such is proven and established.

Alternatively, the fixing of the at least one connecting portion of the filter medium to the wall of the bioreactor can be performed by bonding.

BRIEF DESCRIPTION OF THE DRAWINGS

Further features and advantages of the invention will become apparent from the description below and from the accompanying drawings to which reference is made and in which.

DETAILED DESCRIPTION OF THE INVENTION

The figures exemplarily show how a filter pocket can be formed in a large bioreactor. More specifically, FIGS. 1 to 3 refer to a first embodiment of a bioreactor having a total volume of 100 liters (recommended working volume: 50 liters), FIGS. 4 to 6 to a second embodiment of a bioreactor having a total volume of 200 liters (recommended working volume: 100 liters). The description below basically applies to both embodiments. The differences between the two embodiments are explained separately at the end.

Figure 1:
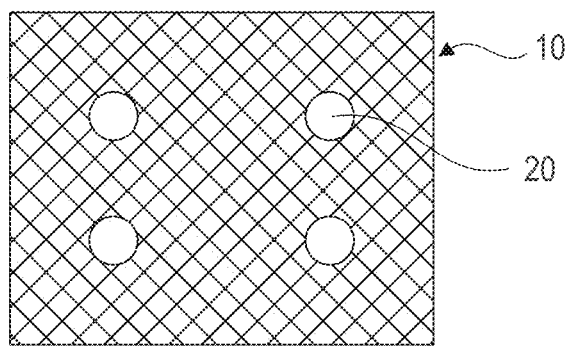
FIG. 1 shows a spacer for a filter pocket in a bioreactor according to the invention in a first embodiment.
Figure 4:
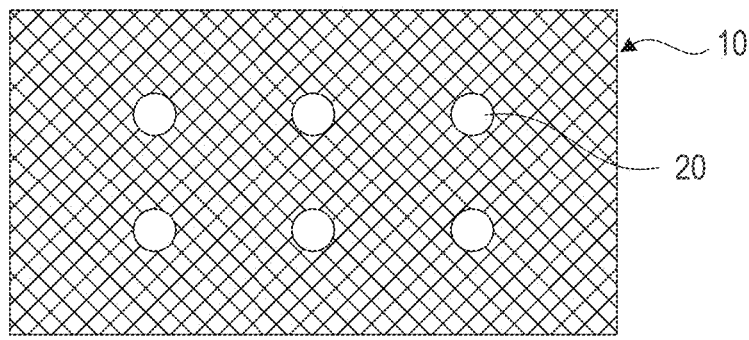
FIG. 4 shows a spacer for a filter pocket in a bioreactor according to the invention in a second embodiment.

FIGS. 1 and 4 each show a blank of a wide-meshed technical textile which serves as a spacer 10 in the finished filter pocket. Preferably, the textile is made of PET-fibers (polyethylene terephthalate), but may also be formed in any other way and/or in any other flexible, break-proof and non-buckling material. It is important that the spacer 10 can be passed through by the filtrated (cell-free) medium in the filter pocket—i.e., is in particular not solid—but is however stable enough to prevent the space defined in the filter pocket from collapsing. Furthermore, it must be ensured that specific areas can be separated out of the spacer 10. This characteristic of the spacer 10 will be discussed in more detail later.

Figure 2:
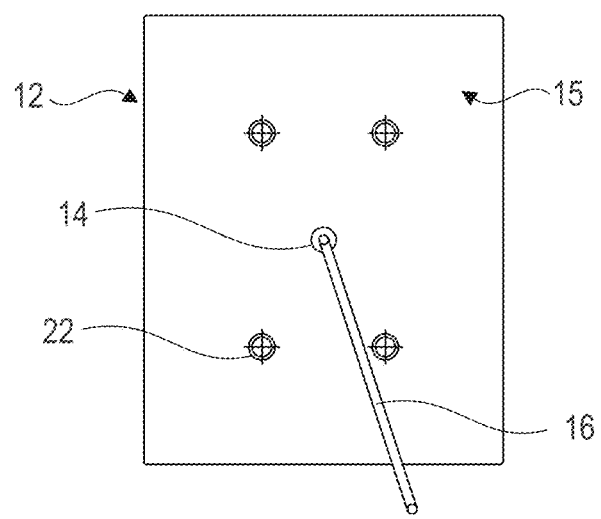
FIG. 2 shows a filter medium for forming a filter pocket in a bioreactor according to the invention in accordance with the first embodiment.
Figure 5:
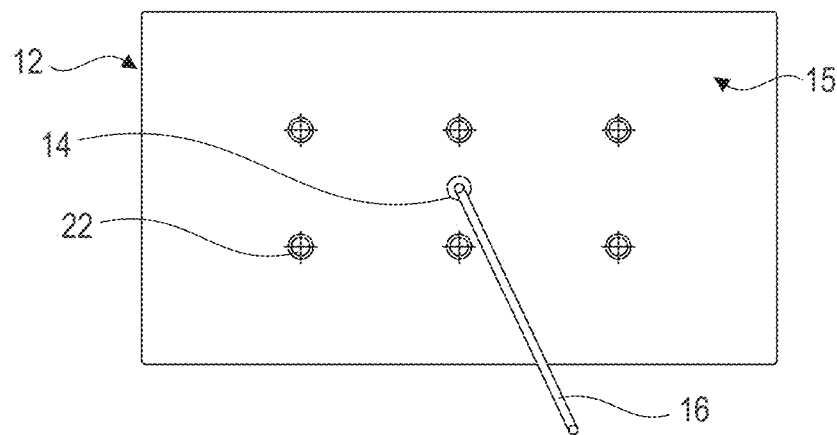
FIG. 5 shows a filter medium for forming a filter pocket in a bioreactor according to the invention in accordance with the second embodiment.

FIGS. 2 and 5 each show a filter medium 12 by means of which the inner wall of the filter pocket in the bioreactor is formed. The filter medium 12 is impermeable to cells, but well permeable to other ingredients of the cell suspension. To this end, microfiltration membranes (only referred to as membranes below) having an effective pore size of 10 µm at maximum are suitable for this purpose, for example a hydrophilic polyethersulfone membrane (PESU) which does not swell upon wetting, having a pore size of 1.2 µm. In any case, the pores are smaller than the meshes of the spacer 10.

One or both sides of the membrane may be adhesively connected to a porous planar structure 15, such as a stable core shroud nonwoven having a PP/PE-PET-PP/PE layered structure (polypropylene/polyethylene-polyethylene terephthalate-polypropylene/polyethylene laminate).

A connecting piece 14 is incorporated in the filter medium 12, for example a hose olive which completely penetrates the filter medium 12. A hose line 16 can be connected to the connecting piece 14 at least on one side of the filter medium 12.

In the following, the manufacture of a filter pocket by means of the filter medium 12 serving as a filter pocket wall and the spacer 10 inside a flexible single-use bioreactor is described by way of example, the wall 18 of which is preferably formed from PE (polyethylene).

The spacer 10 is "perforated" at predetermined locations, i.e., through openings 20 which completely penetrate the spacer 10 are formed at these locations. The through openings 20 can be made in various ways, for example by punching, and in basically any shape, but preferably with a circular circumference. In FIGS. 1 and 4, the spacer 10 is already provided with four and six through openings 20, respectively.

Before the bioreactor is completed, the spacer 10 is first placed on the inner side of the bioreactor wall 18 which faces the culture medium when the bioreactor is in use, at the location where the filter pocket is to be formed, and the larger filter medium 12, which projects beyond the spacer 10 on all sides, is placed thereover.

Subsequently, the edge of the filter pocket wall, which in the example embodiment described here is formed solely from the filter medium 12, is connected to the bioreactor wall 18 in a completely circumferentially fluid-tight manner, in particular by welding. Such a fluid-tight connection is also to be understood as an indirect attachment of the filter pocket wall or the filter medium 12 to the bioreactor wall 18 with material arranged therebetween. An indirect fluid-tight connection may be advantageous, where appropriate, if improved adhesion and/or tightness can be achieved compared to a direct connection. The filter pocket formed in this way, which is not yet finished, is thus delimited on the outside by the bioreactor wall 18 and on the inside (at least partially) by the filter medium 12. The spacer 10 is not involved in this connection step, except that due to the fixing of the edge of the filter medium 12 to the bioreactor wall 18, it is "trapped" in the filter pocket thus formed.

Thereafter, in a further connection step, additional point-like connections are made between the filter medium 12 and the bioreactor wall 18. For this purpose, corresponding connecting portions 22 of the filter medium 12 are pressed through the through openings 20 of the spacer 10 and fixed directly to the bioreactor wall 18. This is possible, for example, by bonding or local heating and fusing, in particular using a spot-welding system. The spacer 10 is not directly involved in this connection step either, i.e., the spacer 10 itself does not form a connection with either the filter medium 12 or the bioreactor wall 18. However, the mobility of the spacer 10 in the filter pocket is severely limited or completely prevented by the point connections, which is advantageous and therefore desirable.

In case of a relatively thick spacer 10 and/or a relatively inflexible filter medium 12, protruding nipples may be provided on the side of the filter medium 12 associated with the bioreactor wall 18, the arrangement of which is adapted to the arrangement of the through openings 20 in the spacer 10. The filter medium 12 is then placed on the spacer 10 prior to fixation such that the nipples extend into or through the through openings 20 to facilitate fixation of the filter medium 12 at these locations. Such nipples may also be provided on the bioreactor wall 18 in addition to, or in place of, the nipples on the filter medium.

The exact shape of the point connections is not of particular importance. For example, annular fastening points can be formed with a heated cylindrical tube.

It is however important that the point connections are not arranged in the edge region, but in a central region of the filter medium 12. This not only ensures that the connection between the filter medium 12 and the bioreactor wall 18 is significantly strengthened, but also that the spacer 10 is fixed in position without being directly involved in the connection between the filter medium 12 and the bioreactor wall 18. The individual point connections also ensure that no chambers or other dead spaces are separated or delimited within the filter pocket. Rather, the medium can reach any region of the filter pocket.

Figure 3:
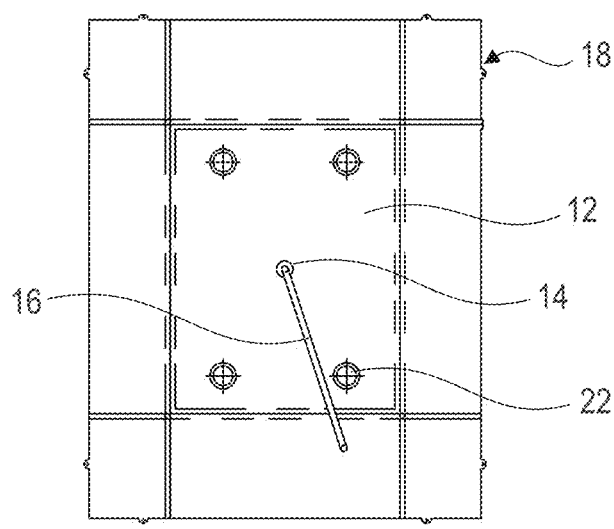
FIG. 3 shows a finished filter pocket in a bioreactor according to the invention in accordance with the first embodiment.
Figure 6:
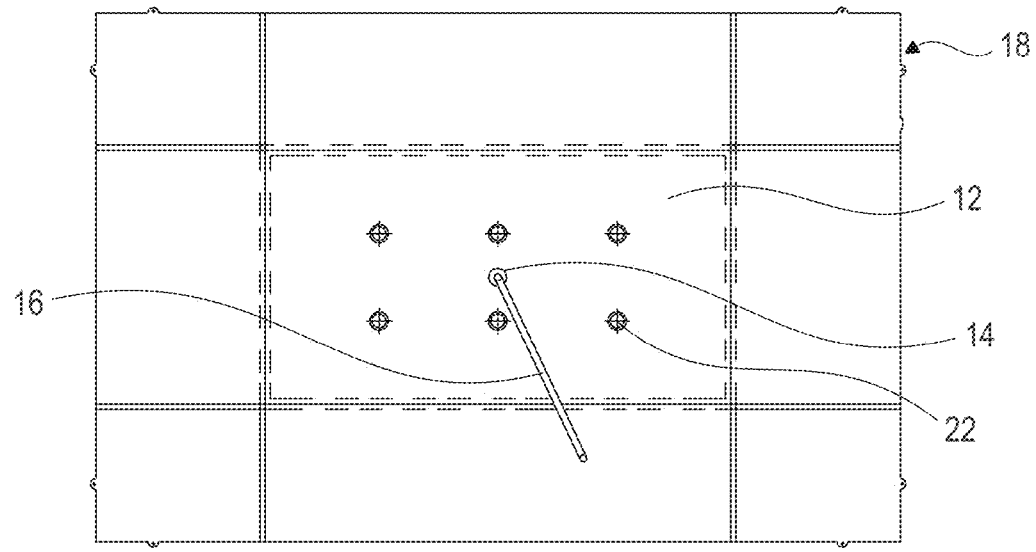
FIG. 6 shows a finished filter pocket in a bioreactor according to the invention in accordance with the second embodiment.

As shown in FIGS. 3 and 6, after completion of the two connection steps described above, which in principle can also be carried out in reverse order, a filter pocket suitable for perfusion which is extremely robust is formed in the bioreactor. The bioreactor is then completed in a manner known per se.

The inner filter pocket wall may also be formed only partially of the filter medium 12, i.e., it need not necessarily be formed entirely of the filter medium 12.

The different materials of the filter medium 12, of the spacer 10 and of the bioreactor wall 18 are selected such that the spacer 10—in particular during use of the bioreactor—does not stick either to the filter medium 12 or to the bioreactor wall 18.

A hose line 16 which can be led out of the bioreactor and is provided in particular for discharging medium from the filter pocket can be connected to the connecting piece 14 in the filter medium 12 which faces away from the filter pocket. In principle, other designs are also possible. It is essential that the filter pocket has at least one fluid connection via which a separate flow connection can be realized, which is isolated from the medium in the bioreactor outside the filter pocket, so that the medium to be discharged from the filter pocket does not mix with the remaining medium in the bioreactor.

As mentioned above, FIGS. 1 to 3 refer to a first embodiment of a bioreactor having a total volume of 100 liters, and FIGS. 4 to 6 refer to a second embodiment of a bioreactor having a total volume of 200 liters. In contrast to the first embodiment, not four but six regularly arranged point connections are provided in the second embodiment. However, the specific number, arrangement, shape and size of the point connections are not to be understood as limiting either the embodiments described above or other embodiments, but are in principle variable.

The size, shape and position of the filter pocket in the bioreactor can be largely selected in an arbitrary manner depending on the application. For example, a very elongated filter pocket or even a filter pocket running completely around the inner circumference of the bioreactor are conceivable. In the latter case, a "circumferential" edge connection of the filter pocket wall would be understood as a connection of the two longitudinal edges of the annular filter pocket wall to the bioreactor wall 18.

In general, the specific design of the filter pocket should meet the following requirements and criteria:

On the one hand, the stability of the filter pocket for the respective intended use must be ensured at any time. On the other hand, however, the membrane surface of the filter medium 12 that can be used by flow should be restricted as little as possible, i.e., the filter surface that cannot be used due to the point connections should be as small as possible. In addition, the point connections should impair the distribution of the medium in the filter pocket as little as possible. The function of the connecting piece 14 must also be ensured.

The described concept of manufacturing robust filter pockets has already been successfully tested for bioreactors of the sizes 100 liters and 200 liters for use on a tilting device, but can also be used for bioreactors of other sizes, in particular for even larger bioreactors.

LIST OF REFERENCE NUMERALS 10 spacer
12 filter medium
14 connecting piece
16 hose line
18 bioreactor wall
20 through opening
22 connecting portion

The invention claimed is:

1. A bioreactor for cultivating microorganisms and cells of animal or plant origin, comprising a filter pocket which is arranged on an inner surface of a flexible wall of the bioreactor and which is delimited on an outside by the wall of the bioreactor and on an inside by a filter pocket wall, wherein the filter pocket wall is formed at least partially by a filter medium, and wherein a spacer is arranged in the filter pocket between the flexible wall of the bioreactor and the filter medium,
wherein the spacer has at least one through opening and wherein a connecting portion of the filter medium protrudes through the through opening and is directly connected to the wall of the bioreactor.

2. The bioreactor according to claim 1, wherein a plurality of through openings, which are arranged so as to be regularly distributed over the spacer, is provided, and a plurality of connecting portions of the filter medium protrude through the through opening and are directly connected to the wall of the bioreactor.

3. The bioreactor according to claim 1, wherein the filter pocket is free of completely er partially separated chambers.

4. The bioreactor according to claim 1, wherein the wall of the bioreactor is at least partially formed of polyethylene.

5. The bioreactor according to claim 1, wherein the spacer is at least partially formed of polyethylene terephthalate.

6. The bioreactor according to claim 1, wherein the filter medium is a microfiltration membrane which is at least partially formed of polyethersulfone.

7. The bioreactor according to claim 6, wherein at least one of two sides of the microfiltration membrane is connected to a porous planar structure.

8. The bioreactor according to claim 7, wherein the porous planar structure is a polypropylene/polyethylene-polyethylene terephthalate-polypropylene/polyethylene laminate.

9. The bioreactor according to claim 1, wherein a connecting piece to which a hose line can be coupled is inserted into the filter medium.

10. The bioreactor according to claim 1, wherein the bioreactor has a maximum total volume of at least 50 liters.

11. The bioreactor according to claim 10, wherein the maximum total volume is at least 100 liters.

12. The bioreactor according to claim 10, wherein the maximum total volume is at least 200 liters.

13. The bioreactor according to claim 1, wherein the direct connection between the connecting portion of the filter medium and the wall of the bioreactor is a bonding or spot welding connection, wherein the spacer does not form part of the direct connection.

14. A method of manufacturing a filter pocket in a bioreactor for cultivating microorganisms and cells of animal or plant origin, comprising the following steps:
providing a flexible wall for forming a bioreactor, a spacer, and a filter pocket wall formed at least partially by a filter medium, wherein the filter pocket wall has a greater superficial extent than the spacer;
forming at least one through opening in the spacer which completely penetrates the spacer;
placing the spacer on an inner surface of the flexible wall of the bioreactor;
placing the filter pocket wall on the spacer;
circumferentially fixing an edge of the filter pocket projecting beyond the spacer to the wall of the bioreactor;
passing a connecting portion of the filter medium through the through opening; and
fixing the connecting portion of the filter medium directly to the wall of the bioreactor.

15. The method according to claim 14, wherein the fixing of the at least one connecting portion of the filter medium to the wall of the bioreactor is performed by spot welding.

16. The method according to claim 14, wherein the fixing of the at least one connecting portion of the filter medium to the wall of the bioreactor is performed by bonding.

* * * * *